(12) United States Patent
Atzinger et al.

(10) Patent No.: US 10,779,781 B2
(45) Date of Patent: Sep. 22, 2020

(54) MEDICAL EXAMINATION OR TREATMENT FACILITY, COMPRISING A C-ARM

(71) Applicant: Siemens Healthcare GmbH, Erlangen (DE)

(72) Inventors: Michael Atzinger, Seybothenreuth (DE); Stefan Gross, Trabitz (DE); Berthold Baumann, Kastl (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 115 days.

(21) Appl. No.: 15/980,788

(22) Filed: May 16, 2018

(65) Prior Publication Data

US 2018/0333116 A1 Nov. 22, 2018

(30) Foreign Application Priority Data

May 19, 2017 (DE) .................. 10 2017 208 530

(51) Int. Cl.
*A61B 6/00* (2006.01)
*B25J 18/00* (2006.01)
*B25J 11/00* (2006.01)
*B21D 53/18* (2006.01)

(52) U.S. Cl.
CPC .......... *A61B 6/4458* (2013.01); *A61B 6/4441* (2013.01); *B21D 53/18* (2013.01); *B25J 11/00* (2013.01); *B25J 11/008* (2013.01); *B25J 18/005* (2013.01); *Y10S 901/27* (2013.01); *Y10S 901/31* (2013.01)

(58) Field of Classification Search
CPC .. H05G 1/02; B21D 53/18; B25J 11/00; B25J 11/008; B25J 18/005; Y10S 901/27; Y10S 901/31; A61B 6/44; A61B 6/4428; A61B 6/4458; A61B 6/4441; A61B 6/4411; A61B 6/4435; A61B 6/4275; A61B 6/4266; A61B 6/587–589
See application file for complete search history.

(56) References Cited

U.S. PATENT DOCUMENTS

| 4,769,832 | A | * | 9/1988 | Louiday | A61B 6/4441 378/193 |
| 2009/0185662 | A1 | * | 7/2009 | Gross | A61B 6/4441 378/197 |
| 2012/0314843 | A1 | | 12/2012 | Limmer et al. | |

(Continued)

FOREIGN PATENT DOCUMENTS

| DE | 4111780 A1 | 10/1992 |
| DE | 202011002199 U1 | 4/2011 |
| DE | 102011077086 A1 | 12/2012 |

OTHER PUBLICATIONS

German Office Action dated Nov. 14, 2017 for German Application No. 10 2017 208 530.4.

*Primary Examiner* — Prasad V Gokhale
(74) *Attorney, Agent, or Firm* — Harness, Dickey & Pierce, P.L.C.

(57) ABSTRACT

A medical examination or treatment facility includes a C-arm, arranged on a support bracket of a robot configured to move the C-arm in space. In an embodiment, the C-arm is made up of a plurality of arm elements in the form of sheet metal parts and at least one coupling unit including at least one cast metal part for coupling the C-arm to the support bracket.

19 Claims, 4 Drawing Sheets

(56) References Cited

U.S. PATENT DOCUMENTS

| | | | |
|---|---|---|---|
| 2015/0164441 A1* | 6/2015 | Niizeki | H05G 1/02 |
| | | | 378/11 |
| 2015/0216494 A1* | 8/2015 | Atzinger | H01L 27/14601 |
| | | | 378/15 |
| 2017/0202529 A1* | 7/2017 | Baumann | A61B 6/4476 |
| 2017/0258427 A1* | 9/2017 | Risher-Kelly | A61B 6/035 |
| 2019/0150865 A1* | 5/2019 | Johnson | A61B 6/4441 |

* cited by examiner

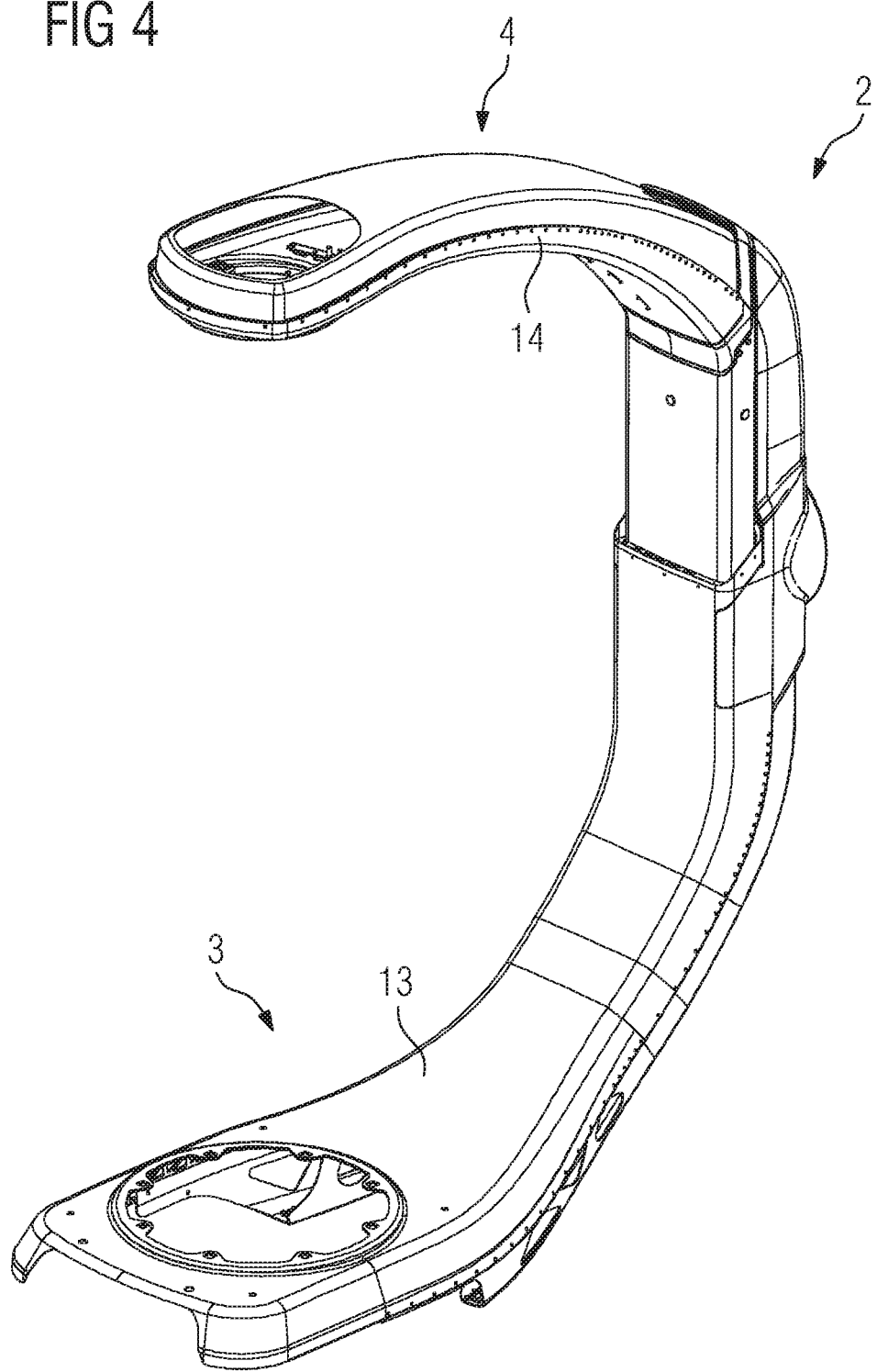

MEDICAL EXAMINATION OR TREATMENT FACILITY, COMPRISING A C-ARM

PRIORITY STATEMENT

The present application hereby claims priority under 35 U.S.C. § 119 to German patent application number DE 102017208530.4 filed May 19, 2017, the entire contents of which are hereby incorporated herein by reference.

FIELD

At least one embodiment of the invention generally relates to a medical examination or treatment facility, comprising a C-arm, which is arranged on a support bracket of a robot moving the C-arm in space.

BACKGROUND

Such medical examination or treatment facilities are used for example in the fields of angiography, cardiology and neurology. They comprise a C-arm, at one end of which a radiation facility, generally an X-ray emitter, is arranged, with a radiation receiver at the opposite end. The C-arm itself is arranged on a support bracket of a robot moving the C-arm in space, said robot generally being mounted on the floor. The support bracket itself is a support bracket with multiple axes, having for example six adjustment axes. There are therefore six degrees of freedom of movement, allowing the arm to be moved along almost any tracks in space and offering a wide spectrum of positioning options or movement options, including orbital movement.

To fasten the C-arm to the support bracket a corresponding fastening flange is generally provided on the support bracket, the C-arm being mounted thereon using a corresponding fastening interface or coupling unit. In order not to restrict the movement space too much with the robot and support bracket, in other words in order to restrict the movement kinematics as little as possible, attempts are made to ensure that the robot or support bracket are as small as possible, in other words to keep the robot dimensions small. Counter to this is the requirement that the support bracket payload should be as large as possible, as the C-arm and attachments (radiation source, radiation receiver, supply lines, etc.) are extremely heavy. The C-arm itself is generally a cast aluminum part with a corresponding framework structure, in the interior of which the supply lines are passed and at the ends of which the imaging components are arranged, the heaviest component of these being the radiation source. The considerable inherent weight of all the arm elements means that the maximum payload limit is reached relatively quickly, which in turn is offset by correspondingly large dimensions of robot and support bracket.

A C-arm for a C-arm X-ray device is known from DE 20 2011 002 199 U1. The C-arm consists of steel sheets that have been welded together and form the C-arm profile of the C-arm. It is a hollow profile with grooves that are open to the outside at the sides along the C-arm shape, the guide rollers of the support or adjusting facility, along which the C-arm can be adjusted, being held or guided therein.

A method for producing a ring-shaped or curved metal part, which can be a C-arm of an X-ray examination device, is known from DE 41 11 780 A1. Here a sheet metal is bent into a ring and the ends of the sheet are connected, so that elevations or depressions running around the sheet metal ring thus formed can be shaped by rollers arranged inside or outside the sheet metal, their interacting profiles being tailored to the elevations or depressions to be produced. During the shaping process the rollers are moved simultaneously in a radial direction and parallel to the axis of the sheet metal ring in such a manner that the sheet metal ring is only stretched or compressed in a radial direction. This allows the necessary stability to be produced at the periphery of the shaped part by way of the elevations or depressions.

Finally DE 10 2011 077 086 A1 discloses a C-arm X-ray device with driven C-arm bearing rollers. The X-ray device comprises a drive unit for moving and stopping the C-arm by means of bearing rollers, on which the C-arm is supported in a movable manner, the drive unit being actively connected to the bearing rollers. The C-arm can also be moved along the fixed support.

SUMMARY

At least one embodiment of the invention specifies an improved medical examination or treatment facility.

In at least one embodiment of the invention, provision is made with a facility for the C-arm to be made up of a number of arm elements in the form of sheet metal parts and at least one coupling unit comprising at least one cast metal part for coupling the C-arm to the support bracket.

According to at least one embodiment of the invention, it is proposed that the C-arm is predominantly made of sheet metal parts and at least one cast metal part is only provided for the coupling unit, forming the interface for the support bracket. In other words no further cast metal part is used apart from the coupling unit, the brackets or arm segments extending on both sides of the coupling unit only being formed by corresponding sheet metal parts. This means that the C-arm itself can be much lighter than was the case with previously known arms with a cast aluminum framework structure, as the sheet metal parts are much lighter in weight and it is possible to achieve very large payloads by designing the component geometry and arrangement appropriately, so that the arm is extremely stable per se and at the same time low in weight.

BRIEF DESCRIPTION OF THE DRAWINGS

Further advantages and details will emerge from the example embodiments described in the following as well as from the drawings, in which:

FIG. 4 shows the fully mounted C-arm from FIG. 2, but without outside cladding parts.

DETAILED DESCRIPTION OF THE EXAMPLE EMBODIMENTS

Figure 1:
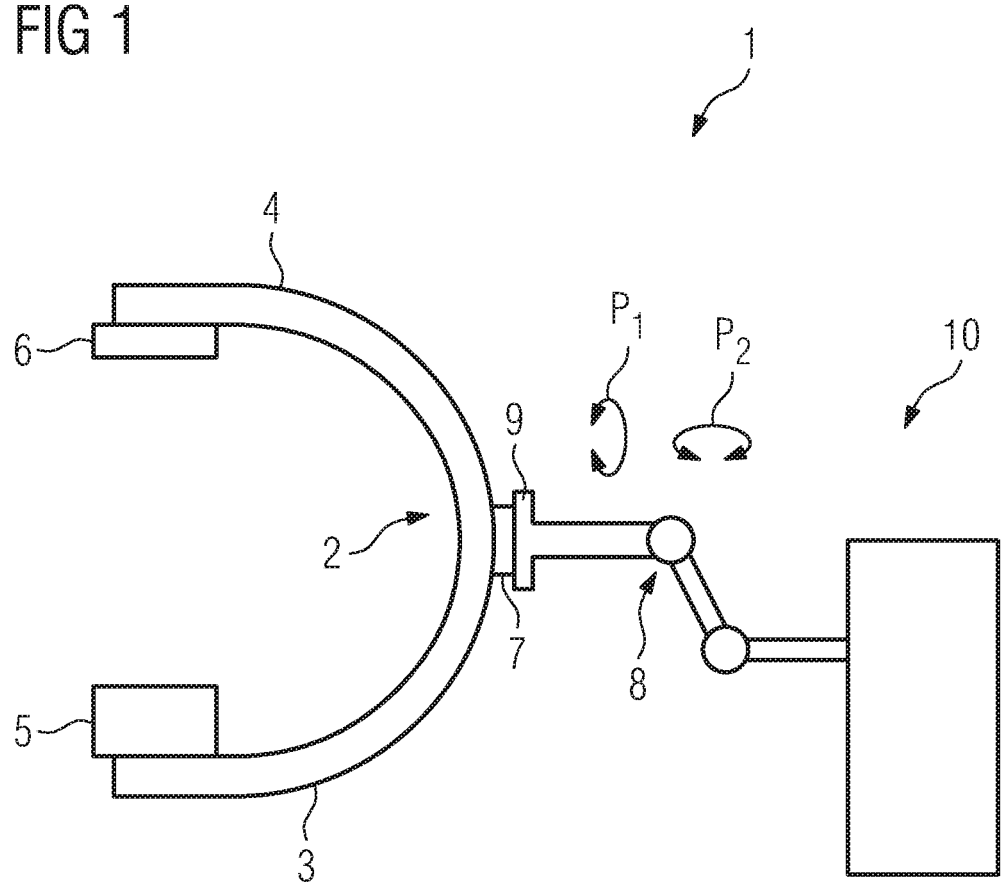
FIG. 1 shows an outline view of an example embodiment of an inventive medical examination or treatment facility.

In the following, embodiments of the invention are described in detail with reference to the accompanying drawings. It is to be understood that the following description of the embodiments is given only for the purpose of illustration and is not to be taken in a limiting sense. It should be noted that the drawings are to be regarded as being schematic representations only, and elements in the drawings are not necessarily to scale with each other. Rather, the representation of the various elements is chosen such that their function and general purpose become apparent to a person skilled in the art.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment of the invention, provision is made with a facility for the C-arm to be made up of a number of arm elements in the form of sheet metal parts and at least one coupling unit comprising at least one cast metal part for coupling the C-arm to the support bracket.

According to at least one embodiment of the invention, it is proposed that the C-arm is predominantly made of sheet metal parts and at least one cast metal part is only provided for the coupling unit, forming the interface for the support bracket. In other words no further cast metal part is used apart from the coupling unit, the brackets or arm segments extending on both sides of the coupling unit only being formed by corresponding sheet metal parts. This means that the C-arm itself can be much lighter than was the case with previously known arms with a cast aluminum framework structure, as the sheet metal parts are much lighter in weight and it is possible to achieve very large payloads by designing the component geometry and arrangement appropriately, so that the arm is extremely stable per se and at the same time low in weight.

The sheet metal parts themselves are preferably deep-drawn parts, which have been shaped appropriately from a flat metal sheet using a deep-drawing method. The cast metal parts themselves are preferably precision cast steel parts, which are generally produced using an expendable mold. The wall thickness of the sheet metal or deep-drawn parts here should be between 1.0-3.0 mm, while the wall thickness of the cast metal or precision cast steel parts should be at least 3 mm to several centimeters. A greater wall thickness is required in cast part segments where for example screw threads or the like are to be introduced than in other segments only present for reinforcing or geometric purposes.

In one expedient development of at least one embodiment, the sheet metal parts themselves, which as described form the actual arm brackets extending to the left and right of the coupling unit, comprise a number of shell parts and reinforcing parts. The shell parts here expediently comprise inner shell and outer shell parts, between which one or more reinforcing parts is/are arranged. The inner and outer shell parts therefore form a hollow space, in which the reinforcing part(s) is/are arranged. The shell parts have a corresponding width and an angled edge, by way of which they adjoin one another, forming a corresponding hollow space in which the reinforcing part(s) is/are then arranged.

Different rigidity and strength requirements are set for the C-arm, depending on the components the respective bracket or arm segment is to support. The one bracket or part of the C-arm supports the radiation receiver, generally a solid-state image detector, which does not have too great a weight. For this reason it can be configured with a simple structure. To this end a reinforcing part can be arranged standing vertically in relation to the inner and outer shell parts at least in one bracket of the C-arm, extending at least partially around the periphery of the bracket. Ultimately a minimum of only three parts is used here, specifically the curved inner and outer shells and the similarly slightly curved reinforcing part, in some instances also a number of reinforcing parts. This reinforcing part stands vertically in relation to the shell parts, forming as it were a type of bulkhead partition in the interior of the hollow space delimited by the shell parts. This is sufficient for this bracket, which supports the radiation receiver for example.

The other bracket or arm segment, as described, supports the radiation source, in other words for example the X-ray emitter, an extremely heavy component. In order to configure this bracket so that it is sufficiently rigid and strong, provision is made for a reinforcing part that corresponds to the shape of the inner and outer shell parts to be arranged between these at least in one bracket of the C-arm. Provision is therefore made here for a multilayer structure, in the simplest instance comprising the two shell parts and the shape-compatible reinforcing part present between them. This reinforcing part can be provided for example with corresponding recesses, producing a type of rib structure or the like. This reinforcing part increases the stability and rigidity of said bracket, allowing even heavy loads to be supported.

It is expedient in this context for the shell parts to curve outward, in other words for there to be an approximately oval cross section, as the shell parts are relatively wide, as described, compared with the edge segments. According to the invention the wide center segments now curve outward, producing an approximately oval hollow space cross section. This curvature also enhances stability.

The coupling unit itself serves on the one hand for coupling to the support bracket but also to hold and fix the arm brackets, formed from the sheet metal parts or shell and reinforcing parts. In one expedient development of the invention provision can be made for the coupling unit to comprise a first cast metal part, which serves for connection to the support bracket and on which a first part of the sheet metal parts is arranged, and a second cast metal part, which is connected to the first cast metal part in a linearly movable manner and on which a second part of the sheet metal parts is arranged.

According to at least one embodiment of the invention, the geometry of the C-arm can be varied, in that the two brackets or arm segments can be moved linearly relative to one another. To this end two cast metal parts are provided, one of which is fastened to the support bracket, therefore in a fixed position, meaning that the bracket or arm segment fastened thereto is also in a fixed position. The second cast metal part is arranged on this first cast metal part in such a manner that it can be adjusted by way of corresponding linear guides, to which end a corresponding roller support, for example a circulating ball bearing support or the like, is provided. Adjustment can be performed for example by means of a spindle drive or the like, which is arranged between the cast metal parts. The second bracket or arm segment is arranged on this second cast metal part. This allows the distance between radiation source and radiation receiver to be varied as required, standard adjustment paths of up to 30 cm being possible.

Finally provision can be made, in at least one embodiment, for corresponding cladding parts to be provided at least on the outside, cladding at least the brackets or bracket segments formed from the sheet metal parts. In other words corresponding cladding parts, preferably made of plastic, are arranged on the outside of the arm, cladding the sheet metal structure. This would also be possible on the inside but it is not essential there, as the inner shell parts preferably have a closed surface, in other words do not have recesses or the like, and therefore form an arm inner surface that is very easy to clean without the need for additional cladding.

Any cables or supply lines can either be passed in the interior of the arm structure or in the region between the outer shell part and the respective cladding part.

The support bracket itself is preferably a 6-axis support bracket, in other words a bracket with six degrees of freedom of movement by way of corresponding rotating or pivoting articulations, allowing extremely variable arm adjustment in space.

FIG. 1 shows an outline view of a medical examination or treatment facility 1 of an example embodiment, comprising a C-arm 2 with a first bracket 3 and a second bracket 4, the first bracket 3 in the illustrated example supporting a radiation source 5 and the second bracket 4 supporting a radiation receiver 6.

The C-arm 2 also comprises a coupling unit 7, by way of which it is fastened to a support bracket 8, which has a corresponding fastening flange 9. The support bracket 8 is part of a robot 10, by way of which the C-arm 2 and therefore also the imaging components (radiation source 5, radiation receiver 6) can be moved freely in space. To this end the support bracket 8 can be rotated and pivoted through a plurality of rotation and pivot axes, as indicated by the two double arrows P1 and P2. Generally the support bracket 8 is preferably a 6-axis bracket, in other words there are six degrees of freedom within the movement on the part of the C-arm 2. The structure of such an examination or treatment facility is known in principle.

Figure 2:
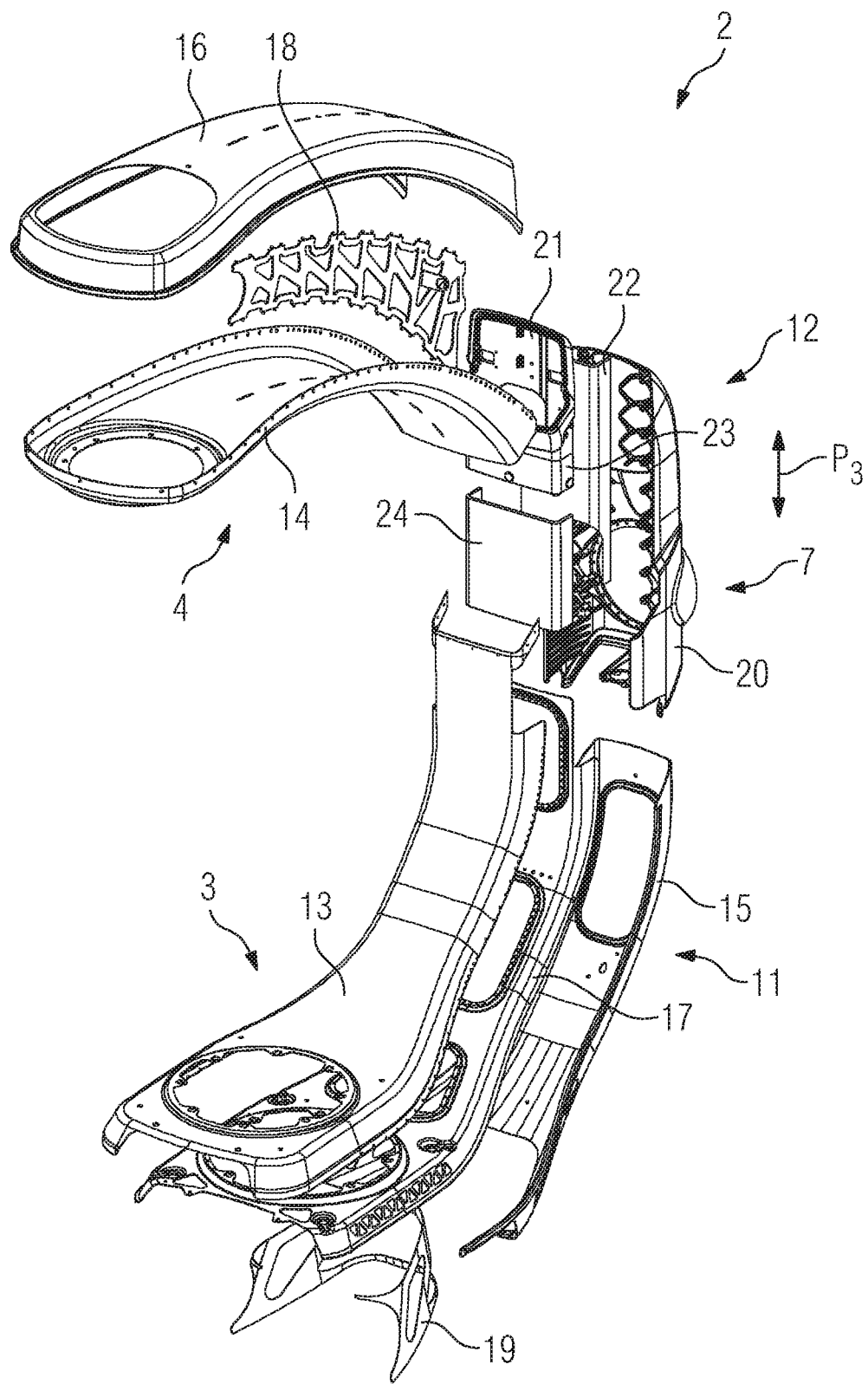
FIG. 2 shows an exploded view of the relevant parts of the C-arm.
Figure 3:
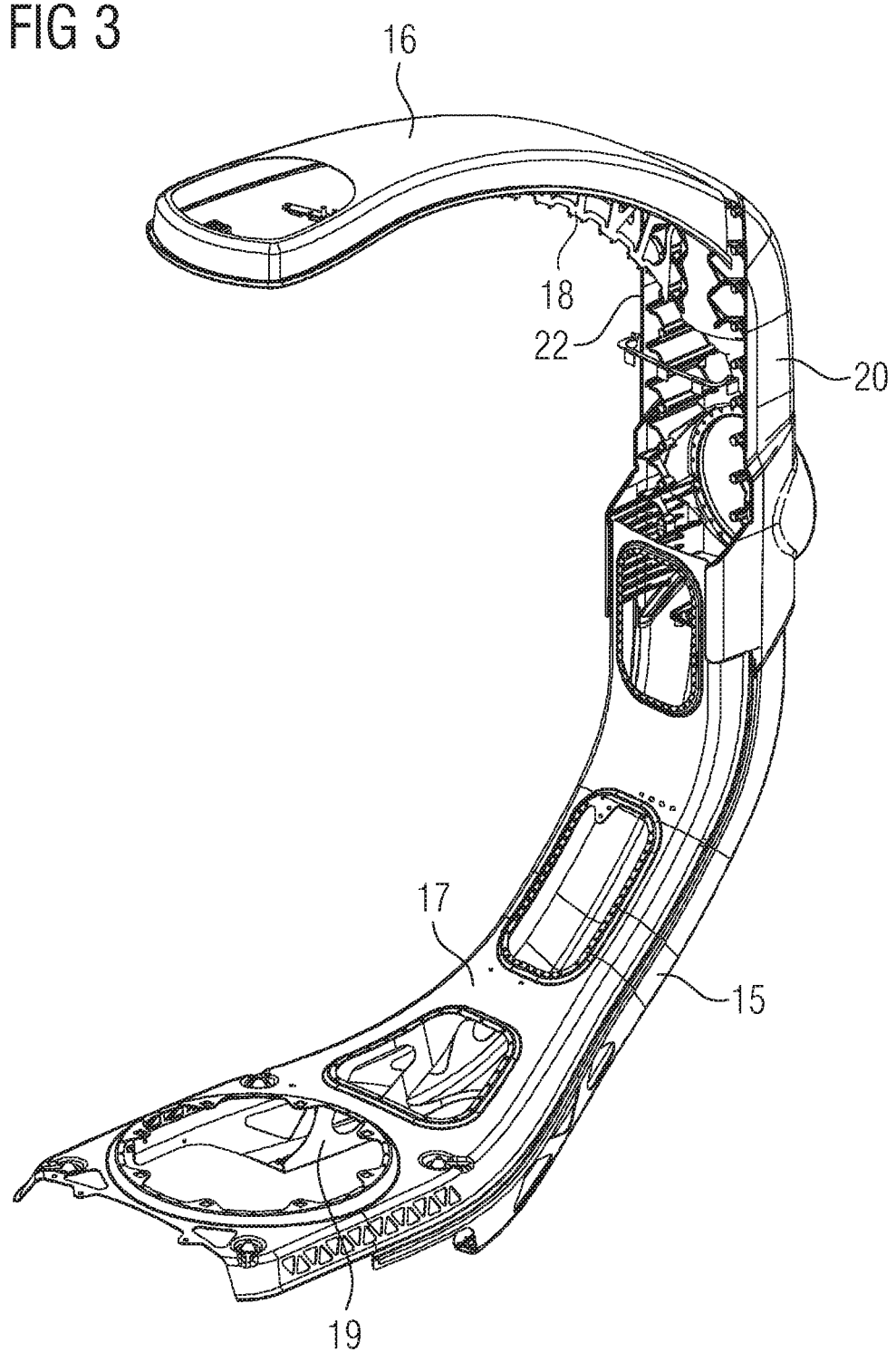
FIG. 3 shows a partially mounted view of the C-arm from FIG. 2.

FIGS. 2-4 show the structure of an example embodiment of an inventive C-arm 2, which is deployed in an example embodiment of the inventive examination or treatment facility 1 from FIG. 1.

FIG. 2 shows an exploded view of the C-arm 2 or its relevant parts. It is made up of a number of sheet metal parts 11 as well as just two cast metal parts 12 in the illustrated example, these forming the actual coupling unit 7. The two bracket segments 3 and 4 are formed by way of the sheet metal parts 11. The sheet metal parts 11 are preferably deep-drawn parts, while the cast metal parts 12 are preferably precision cast steel parts.

Each bracket 3, 4 is made up of an inner shell part 13, 14 and an outer shell part 15, 16, which, see FIG. 2, are ultimately much wider than they are deep. They each have a chamfered edge, with which they adjoin one another, so that they enclose a hollow space. At least one reinforcing part 17, 18 is arranged in said hollow space as well as any supply lines or cables. The shape of the reinforcing part 17 corresponds to the geometry of the inner and outer shells 13, 15, see FIG. 3, where the reinforcing part 17 is shown in the partially mounted position. In contrast in the mounted position the reinforcing part 18 is arranged virtually vertically in relation to the surface segments of the inner and outer shell parts 14, 16, thus forming as it were a type of bulkhead partition and extending some distance around the arm following the periphery between the shell parts 14, 16.

As the bracket 3 supports the much greater load with the radiation receiver 5, a further reinforcing part 19 is additionally provided there, forming a bottom termination, as shown in FIG. 3.

In other words in the illustrated example embodiment the bracket 3 is only made up of four sheet metal parts and the bracket 4 is only made up of three sheet metal parts. They are therefore each made of very few components and therefore very light but also very stable. This is assisted by the fact that the shell parts 13, 14 and 15, 16 have a slightly curved surface, with the result that they enclose an as it were oval hollow space cross section. This curved shape also enhances stability.

The cast metal parts 12 comprise a first cast metal part 20, which provides the actual interface with the support bracket 8 or fastening flange 9. It is in a fixed position. The bracket 3 or all its metal parts 13, 15 and 17 is/are fastened to it. In other words the bracket 3 is also in a fixed position.

Also provided is a second cast metal part 21, which is guided in a linearly movable manner on the first cast metal part 20, allowing vertical movement, as shown by the double arrow P3. The bracket 4 or at least the shell parts 14,16 is/are fastened to the second cast metal part 21, in other words the bracket 4 can also be moved vertically. This allows the distance between the radiation source 5 and the radiation receiver 6 to be varied as required.

To allow such linear movement, corresponding linear guides 22, 23 are provided on the cast metal parts 20, 21, for example corresponding roller or slide bearing guides or the like and a corresponding positioning facility, for example in the form of a spindle drive or the like, is of course also provided between these cast metal parts 20, 21.

Finally a slide or cover sheet metal part 24 is shown, which covers the region of the linear guides and with which a slide (not shown in detail) fastened to the bracket 4 or the second cast metal part 21 interacts, thus preventing the ingress of dirt into the region.

FIG. 3 shows a partially mounted view, in which the first cast metal part 20 as well as the outer shell part 15 fastened thereto and the reinforcing part 17 are fastened. It also shows the second cast metal part 22 and the outer shell part 18 fastened thereto. The reinforcing part 19 is also shown.

Based on FIG. 3 the further components are then mounted, as shown in FIG. 4. Here the inner shell part 13 is also fastened to the bracket 3 and the inner shell part 14 is fastened to the bracket 4, completing the C-arm 2. Shell-type cladding parts (not shown in detail) are only fastened to the curved outside of the arm, so that the arm is clad at this side. There is no need for cladding on the inside of the arm, as it has a large surface that is very easy to clean, as shown in FIG. 4, formed simply by the two sheet metal parts, in other words the corresponding inner shell parts 13, 14.

As described above, the corresponding inner and outer shell parts 13, 14 or 15, 16 have correspondingly chamfered edges. The edges of the inner shell parts 13, 14 here preferably engage over those of the outer shell parts 15, 16. This forms drip rims so that in the unlikely event of liquid running into the inside of the arm, it would be able to drain away over the respective sheet metal surface and drip off the rims in a defined manner, thus preventing any penetration of liquid into the arm interior.

As described, the sheet metal parts are deep-drawn parts, which preferably have a wall thickness of 1.0-3.0 mm, preferably between 1.25 and 2.0 mm. The cast metal parts are precision cast steel parts, which have a minimum wall thickness of approx. 3 mm and of course have greater dimensions in the segments, in which corresponding screw threads or the like are to be introduced. Design is therefore based on the actual mounting requirements.

Although the invention has been illustrated and described in detail using the preferred example embodiment, the invention is not restricted by the disclosed examples and other variations can be derived therefrom by the person skilled in the art, without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A medical examination or treatment facility, comprising:
   a C-arm, arranged on a support bracket of a robot configured to move the C-arm in space, the C-arm including
      a plurality of arm elements formed as sheet metal parts, and
      at least one coupling unit including at least one cast metal part to couple the C-arm to the support bracket.

2. The medical examination or treatment facility of claim 1, wherein the sheet metal parts are deep-drawn parts and wherein the at least one cast metal part include at least one precision cast steel part.

3. The medical examination or treatment facility of claim 2, wherein the sheet metal parts include a plurality of shell parts and reinforcing parts.

4. The medical examination or treatment facility of claim 3, wherein the shell parts include at least one inner shell part and at least one outer shell part, one or more reinforcing parts being arranged between the at least one inner shell part and the at least one outer shell part.

5. The medical examination or treatment facility of claim 4, wherein the one or more reinforcing parts are arranged, standing vertically between the at least one inner shell part and at least one outer shell part, at least in one bracket of the C-arm, extending at least partially around the one bracket of the C-arm.

6. The medical examination or treatment facility of claim 5, wherein at least one reinforcing part, corresponding to a shape of at least one of the at least one inner shell part and at least one outer shell part, is arranged between the at least one inner shell part and at least one outer shell part at least in one bracket of the C-arm.

7. The medical examination or treatment facility of claim 2, wherein the at least one coupling unit includes,
   a first cast metal part, configured to serve for connection to the support bracket, a first part of the sheet metal parts being arranged on the first cast metal part of the coupling unit, and
   a second cast metal part, connected to the first cast metal part in a linearly movable manner, a second part of the sheet metal parts being arranged on the second cast metal part of the coupling unit.

8. The medical examination or treatment facility of claim 1, wherein the sheet metal parts include a plurality of shell parts and reinforcing parts.

9. The medical examination or treatment facility of claim 8, wherein the shell parts include at least one inner shell part and at least one outer shell part, one or more reinforcing parts being arranged between the at least one inner shell part and the at least one outer shell part.

10. The medical examination or treatment facility of claim 9, wherein the one or more reinforcing parts are arranged, standing vertically in between the at least one inner shell part and at least one outer shell part, at least in one bracket of the C-arm, and wherein the one or more reinforcing parts extend, between the at least one inner shell part and at least one outer shell part, at a distance at least partially around the one bracket of the C-arm.

11. The medical examination or treatment facility of claim 10, wherein at least one reinforcing part, corresponding to a shape of at least one of the at least one inner shell part and at least one outer shell part, is arranged between the at least one inner shell part and at least one outer shell part at least in one bracket of the C-arm.

12. The medical examination or treatment facility of claim 9, wherein at least one reinforcing part, corresponding to a shape of at least one of the at least one inner shell part and at least one outer shell part, is arranged between the at least one inner shell part and at least one outer shell part at least in one bracket of the C-arm.

13. The medical examination or treatment facility of claim 9, wherein the at least one inner shell part and at least one outer shell part curve outward.

14. The medical examination or treatment facility of claim 8, wherein the plurality of shell parts curve outward.

15. The medical examination or treatment facility of claim 8, wherein the at least one coupling unit includes,
   a first cast metal part, configured to serve for connection to the support bracket, a first part of the sheet metal parts being arranged on the first cast metal part of the coupling unit, and
   a second cast metal part, connected to the first cast metal part in a linearly movable manner, a second part of the sheet metal parts being arranged on the second cast metal part of the coupling unit.

16. The medical examination or treatment facility of claim 1, wherein the at least one coupling unit includes,
   a first cast metal part, configured to serve for connection to the support bracket, a first part of the sheet metal parts being arranged on the first cast metal part of the coupling unit, and
   a second cast metal part, connected to the first cast metal part in a linearly movable manner, a second part of the sheet metal parts being arranged on the second cast metal part of the coupling unit.

17. The medical examination or treatment facility of claim 1, wherein the sheet metal parts include a wall thickness between 1.0-3.0 mm.

18. The medical examination or treatment facility of claim 1, wherein the at least one cast metal part includes a wall thickness of at least 3 mm.

19. The medical examination or treatment facility of claim 1, wherein the support bracket is a 6-axis support bracket.

* * * * *